United States Patent
Gaertner et al.

(10) Patent No.: US 9,880,083 B2
(45) Date of Patent: Jan. 30, 2018

(54) METHOD AND DEVICE FOR OPERATING A PARTICLE SENSOR

(71) Applicant: Robert Bosch GmbH, Stuttgart (DE)

(72) Inventors: Benjamin Gaertner, Neureut (DE); Andy Tiefenbach, Vaihingen-Horrheim (DE); Mathias Klenk, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 142 days.

(21) Appl. No.: 14/893,764

(22) PCT Filed: May 21, 2014

(86) PCT No.: PCT/EP2014/060403
§ 371 (c)(1),
(2) Date: Nov. 24, 2015

(87) PCT Pub. No.: WO2014/191270
PCT Pub. Date: Dec. 4, 2014

(65) Prior Publication Data
US 2016/0103055 A1    Apr. 14, 2016

(30) Foreign Application Priority Data
May 28, 2013   (DE) .......................... 10 2013 209 872

(51) Int. Cl.
*G01N 15/06* (2006.01)
*F01N 11/00* (2006.01)
(52) U.S. Cl.
CPC ......... *G01N 15/0656* (2013.01); *F01N 11/00* (2013.01); *F01N 2560/05* (2013.01); *F01N 2560/20* (2013.01); *Y02T 10/47* (2013.01)
(58) Field of Classification Search
CPC . G01N 15/0656; F01N 11/00; F01N 2560/05; F01N 2560/20; Y02T 10/47
See application file for complete search history.

(56) References Cited

U.S. PATENT DOCUMENTS

2011/0030451 A1 *   2/2011   Roesch ............... F02D 41/1466
                                                         73/28.02
2011/0047978 A1     3/2011   Zawacki et al.

FOREIGN PATENT DOCUMENTS

CN     102033090 A    4/2011
CN     102421998 A    4/2012
(Continued)

OTHER PUBLICATIONS

International Search Report for Application No. PCT/EP2014/060403 dated Jul. 17, 2014 (English Translation, 2 pages).

*Primary Examiner* — Hezron E Williams
*Assistant Examiner* — David Z Huang
(74) *Attorney, Agent, or Firm* — Michael Best & Friedrich LLP (57) ABSTRACT

The invention relates to a particle sensor (20) for determining a particle content in a gas flow, wherein the particle sensor (20) has, on the surface thereof, at least two interlocking interdigital IDE electrodes (23) and a heating element (26), separated from the IDE electrodes (23) by an insulating layer (21), by means of which heating element the particle sensor (20) can be heated in a regeneration phase and a soot load on the particle sensor can thus be removed, and by means of which particle sensor, in a diagnostic phase during the regeneration phase, a current is measured by intermittently applying a measurement voltage to the IDE electrodes (23) and, based on the chronological progression and size thereof, a functional inspection of the particle sensor (20) is carried out. During the regeneration phase, additional operating phases are introduced, in which, outside of the diagnostic phase (50), ions are specifically moved by intermittently applying specific voltage potentials different from zero volts to the IDE electrodes (23).

17 Claims, 8 Drawing Sheets

(56) References Cited

FOREIGN PATENT DOCUMENTS

| | | |
|---|---|---|
| DE | 10133384 | 1/2003 |
| DE | 102009028239 | 2/2011 |
| DE | 102009028283 | 2/2011 |
| DE | 102012008462 A1 | 10/2012 |
| EP | 1925926 A1 | 5/2008 |
| WO | 2013189806 | 12/2013 |

* cited by examiner

//METHOD AND DEVICE FOR OPERATING A PARTICLE SENSOR

BACKGROUND OF THE INVENTION

The invention relates to a method for operating a particle sensor in order to determine a particle content in a gas flow, wherein the particle sensor comprises on its surface at least two interdigital IDE electrodes engaging in one another and a heating element, which is separated from the IDE electrodes by an insulation layer and by which, in a regeneration phase, the particle sensor can be heated and a soot load on the particle sensor can thereby be removed, and with which, in a diagnostic phase during the regeneration phase, a current is measured by intermittently applying a measurement voltage to the IDE electrodes and, with the aid of the profile and strength of this current as a function of time, a functional test of the particle sensor is carried out.

The invention furthermore relates to a device, in particular a control and evaluation unit, for operating the particle sensor and for carrying out the method according to the invention.

Particle sensors are currently used, for example, to monitor the soot output of internal combustion engines and for on-board diagnosis (OBD), for example for functional monitoring of particle filters. In this case, collecting resistive particle sensors are known, which evaluate a change in the electrical properties of an interdigital electrode structure due to particle deposits. Two or more electrodes may be provided, which preferably engage in one another in the manner of a comb. These are also referred to as interdigital electrodes (IDE). By an increasing number of particles deposited on the particle sensor, the electrodes are short-circuited, which leads to an electrical resistance decreasing with increasing particle deposition, a decreasing impedance or change in a characteristic quantity, such as a voltage and/or a current, associated with the resistance or the impedance. For evaluation, a threshold value, for example of a measurement current between the electrodes, is generally established and the time taken to reach the threshold value is used as a measure of the amount of particles deposited. As an alternative, a signal rate of change during the particle deposition may also be evaluated. When the particle sensor is fully loaded, the deposited particles are burnt in a regeneration phase with the aid of a heating element integrated in the particle sensor.

Such a resistive particle sensor is described in DE 101 33 384 A1. The particle sensor is constructed from two comb-like electrodes engaging in one another, which are at least partially covered with a trapping sleeve. When particles are deposited from a gas flow on the particle sensor, this leads to an evaluable change in the impedance of the particle sensor, from which the amount of particles deposited and therefore the amount of particles entrained in the exhaust gas can be deduced.

In the resistive particle sensor, the self-diagnosis of the interdigital electrodes (IDE) is based on a current measurement at elevated temperatures. Owing to the presence of sodium ions in the insulation layer under the electrode, there is in this case a certain measurable electrical conductivity. This diagnosis is therefore carried out during the sensor regeneration, during which active heating is carried out anyway and temperatures >750° C. are reached. According to the prior art, the negative IDE electrode (IDE−) is grounded during this phase, as is the positive IDE electrode (IDE+) except for the short diagnostic phase, for which reason the positive heating element terminal and parts of the heating element always have a positive electrical potential relative thereto during operation.

Since the regeneration, during which soot particles are burnt, typically lasts many seconds to minutes, positively charged particles, particularly the $Na^+$ ions, experience a driving force from the interior of the sensor, where the heating element is located, to the surface where the IDE electrodes lie, for this prolonged time. Because of the high sensor temperature during this phase, the $Na^+$ ions have a high mobility and migrate upward toward the surface of the particle sensor. Furthermore, on the surface and in layers near the surface, the $Na^+$ ions experience a driving force toward the negative IDE electrode (IDE−) during phases in which a positive potential is applied to the positive IDE electrode (IDE+) and the sensor temperature is still high. This is the case during the self-diagnosis itself as well as at the start of a measurement phase, the sensor temperature being less in this case than during the regeneration.

On the surface, and to an increased extent in the vicinity of the negative IDE electrode (IDE−), concentration of the $Na^+$ ions ultimately takes place. Exhaust gas condensate, or water, which passes through the sensor when starting the engine until the dew point end (DPE) or condenses on the electrodes during cooling of the exhaust gas system, washes out the ions or sodium compounds resulting therefrom, particularly during a cold start. Because of the subsequent temperature rise during the sensor operation, evaporation takes place, which ultimately leads to loss of the $Na^+$ ions which are only present to a limited extent. Since, by principle, this sensor regeneration and the self-diagnosis take place periodically, and therefore often, corresponding ageing is to be expected, which may possibly lead to failure of the statutorily prescribed self-diagnosis possibility of the electrodes within the intended lifetime. Migration of the $Na^+$ ions to the electrode, and particularly toward the negative IDE electrode (IDE−), and ultimately loss thereof over the lifetime, cannot therefore be prevented. Conversely, in the case of systems with exhaust gas systems in which $Na^+$-rich exhaust gas condensates occur, it is also possible that $Na^+$ ions will enter the sensor element and accumulate there. With an increasing amount, the $Na^+$ ions cause interference. In the worst case, this can lead to detection of a shunt, and therefore to a sensor defect. Other ions, for example $K^+$ ions, can likewise lead to the same effect and be treated correspondingly.

In a subsequent sensor generation, the sensor self-diagnosis is based no longer on the $Na^+$ ion conduction but on electronic conductivity. This is achieved by doping the insulation layer under the IDE electrodes with iron during production of the sensor, and can be measured at comparable temperatures during operation. In this case, ions are nevertheless contained in these layers and can cause interference, particularly when ions are additionally introduced from the outside as described above.

DE 10 2009 028 239 A1 describes a method and a device for diagnosing a collecting particle sensor with a substrate, two interdigital electrodes and a heating element. The diagnosis is carried out at high temperatures by means of a current measurement between the electrodes, the flow of current taking place through a semiconducting layer arranged under the electrodes. The charge transport itself takes place by means of mobile ions, particularly by means of sodium ions, which are introduced into the substrate by impurities during the production process or by deliberate doping, and which form from the semiconducting layer. In one embodiment, the diagnosis is carried out with AC voltage, which prevents polarization. When a DC voltage is used, the decrease in the conductivity due to polarization effects is detected. For regeneration, a subsequent heat treatment is provided, by which a uniform distribution of the ions is re-established. It is furthermore proposed to apply a recharging pulse lasting from 1 to 1000 ms with a voltage of about −10 V DC, in order to achieve active regeneration. The described method in this case relates to the diagnostic phase.

It is therefore an object of the invention to introduce new types of operation, or operating phases, during phases in which the particle sensor is not in the measurement mode but has elevated temperatures, i.e. particularly during the sensor regeneration, in order deliberately to displace the $Na^+$ ions so as to prevent loss of these ions or, in the event of an excess of $Na^+$ ions in the sensor element in the close vicinity of the IDE electrodes, to deliberately displace them away, preferably permanently, deep into the bulk or deliberately to an electrode on the surface.

It is furthermore an object of the invention to provide a corresponding device for carrying out the method, in particular a control and evaluation unit.

SUMMARY OF THE INVENTION

The object relating to the method is achieved in that, during the regeneration phase, additional operating phases are introduced in which, outside the diagnostic phase, ions are deliberately displaced by intermittently applying certain voltage potentials different to zero volts to the IDE electrodes. With the proposed method, cations, in particular $Na^+$ ions, can be deliberately displaced in order to prevent their loss over the lifetime due to leaching processes during operation or, in the case of an increased input of $Na^+$ ions into the element, for example by means of the exhaust gas condensate, to displace them deliberately into regions where they do not cause interference. In this way, the lifetime of the particle sensors can be extended. Furthermore, ion concentrations in the near-surface regions of the IDE electrodes may be provided at least intermittently, as preparation for the diagnostic phase, so that self-diagnosis of the particle sensor can be carried out without interference. Furthermore, in the event of an excess of ions in the region under the electrodes, an unintentionally high ionic conductivity and therefore sensor malfunction can be prevented.

If, as in a preferred method variant, for a particular predeterminable time during a polarization reversal phase preceding the diagnostic phase, a positive voltage potential is applied to the negative IDE electrode, the positive IDE electrode being at a ground potential, it is possible to achieve the effect that, by electrode repoling, $Na^+$ ions which, by principle, are driven toward the negative electrode during the self-diagnosis, or have previously concentrated there, are displaced back toward the otherwise positive electrode. This is advantageous when it takes place shortly before the diagnostic phase, in order to avoid a polarization effect which may otherwise negatively influence the self-diagnosis. The distribution of the $Na^+$ ions can be adjusted in a controlled way through the length of the polarization reversal phase.

In order not to significantly lengthen the overall cycle time of the particle sensor, however, only short polarization reversal phases of at most 1 s should be provided. Because of the small spacings of the electrode fingers, this period of time is generally sufficient. Since the return polarization and the polarization during the diagnostic phase should in the ideal case compensate for one another, it is advantageous for a duration which corresponds at most to the duration of the diagnostic phase to be selected for the polarization reversal phase.

According to another preferred method variant, in further operating phases during the regeneration phase, outside the diagnostic phase and the polarization reversal phase, the electrical potentials of the IDE electrodes are set to be equal to or greater than a heating element voltage (typically, this lies between +8 and +13 V). These further operating phases may be used as an alternative to the polarization reversal phase or in combination therewith. In this way, the ions, particularly the easily displaceable $Na^+$ ions in the layer regions between the IDE electrodes and the heating element, which are important for diagnostic purposes experience a driving force in the opposite direction and can be driven back into the bulk of the particle sensor by this measure in contrast to the prior art. By means of the value of the voltage and the duration, it is possible to adjust the penetration depth of the ions or the distribution in the bulk.

In this case, provision may be made that, during these operating phases, the negative IDE electrode can be switched between a floating voltage potential and a voltage potential higher than the positive heating element voltage, and the positive IDE electrode is operated during this time with a voltage potential equal to or higher than the positive heating element voltage. In this way, the ageing behavior as described in the introduction can be positively influenced by the minimization thereby possible of the concentration of $Na^+$ ions on the sensor surface in the region of the IDE electrodes. Furthermore, there are no negative effects on the result of the self-diagnosis during the diagnostic phase. It is thereby even possible to achieve preconditioning in terms of optimal ion concentration conditions for the diagnostic phase.

It has been found advantageous for the voltage potential at the positive IDE electrode to be between +8 and +13 volts, which corresponds to the typical heating element voltage, or more than +40 V, typically +45.6 V.

According to a preferred method variant, the voltage potentials at the IDE electrodes, with the exception of the diagnostic phase and the polarization reversal phase, are applied throughout the entire regeneration phase or intermittently. The distribution in the bulk of the particle sensor can be adjusted in a controlled way by means of the duration of the potential conditions set up. Since the phase of burning out typically lasts many seconds to minutes, these operating phases can be used for a long time during the regeneration phase of the particle sensor.

In one operating variant, provision may be made that, in terms of the voltage potentials applied to the IDE electrodes and duration, the additional operating phases within the regeneration phase of the particle sensor are fixed in advance or adapted as a function of the present state of the IDE electrodes. Since the diagnostic current during the diagnostic phase is based on charge carriers which have good mobility at higher temperatures, as is the case particularly for $Na^+$ ions, as a function of its present strength or its variation over the lifetime, it may be reduced, increased or kept constant by deliberate variation of the IDE potentials, for example. With this adaptation, in particular, a diagnostic current decreasing over the lifetime may be counteracted or, in the event of an excess of ions, a sensor malfunction may be prevented.

A preferred use of the method and its variants as described above provides the operation of a particle sensor in the scope of on-board diagnosis of the particle sensor, which is arranged in the exhaust gas system of an internal combustion engine configured as a diesel engine or as an Otto engine for on-board diagnosis of a particle filter, or is used for measuring raw soot emissions. In this use, accurate and reproducible diagnosis of the particle loading of the soot particle filter (DPF) arranged in the exhaust gas system of the diesel internal combustion engine is important in particular. On the one hand, premature ageing of the particle sensor due to leaching $Na^+$ ions can be counteracted. On the other hand, optimal concentration conditions for the self-diagnosis of the particle sensor can be achieved. Ageing effects of the diagnostic current measurement can thereby be compensated for, or minimized. Such operating phases may also be used in combustion systems in which a soot concentration or load needs to be monitored with a particle sensor and a self-diagnosis of the functional capability is provided for functional monitoring of the particle sensor.

The object relating to the device is achieved in that the control and evaluation unit comprises instruments, such as an IDE supply unit, an IDE measurement unit, a heating element supply unit and a temperature measurement unit, for carrying out the method according to the method described above and its method variants. Usually, these instruments are already present in control and evaluation units according to the prior art. It is advantageous in this case that no hardware modification has to be carried out on the particle sensor or on the control and evaluation unit in order to carry out the method. This additional functionality can be achieved exclusively by a software supplement. The control and evaluation unit may in this case be configured as an independent unit or as an integral component of a superordinate engine controller.

BRIEF DESCRIPTION OF THE DRAWINGS

The invention will be explained in more detail below with the aid of an exemplary embodiment represented in the figures, in which.

DETAILED DESCRIPTION

Figure 1:
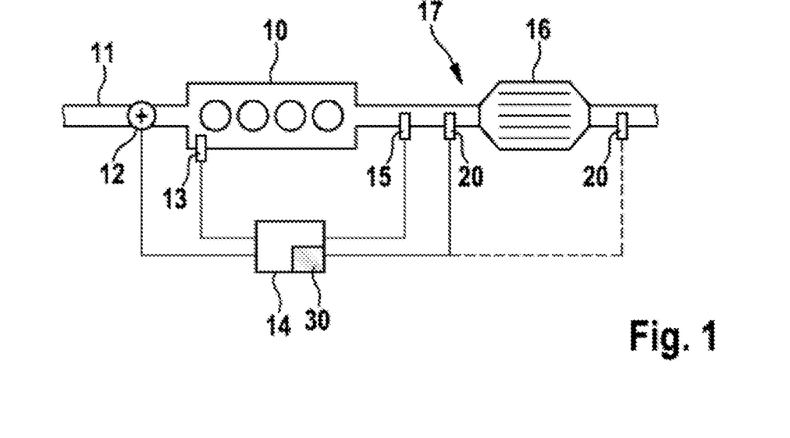
FIG. 1 shows a schematic representation of the technical environment in which the method may be used, FIG. 2 schematically shows a particle sensor in an exploded representation.

FIG. 1 schematically shows the technical environment in which the method according to the invention may be used. An internal combustion engine 10, which may be configured as a diesel engine, is supplied with combustion air via an air feed 11. The quantity of combustion air here may be determined by means of an air mass flow meter 12 in the air feed 11. The quantity of air may be used for correction of a deposition probability of particles present in the exhaust gas of the internal combustion engine 10. The exhaust gas of the internal combustion engine 10 is discharged through an exhaust gas system 17, in which an exhaust gas purification system 16 is arranged. This exhaust gas purification system 16 may be configured as a diesel particle filter. Also arranged in the exhaust gas system 17 are an exhaust gas probe 15 configured as a lambda probe and a particle sensor 20, the signals of which are delivered to an engine controller 14 or a special control and evaluation unit 30 (sensor control unit SCU), which may be configured as a component of the engine controller 14 or as a separate unit. The engine controller 14 is furthermore connected to the air mass flow meter 12 and, on the basis of the data supplied to it, determines an amount of fuel, which can be supplied via a fuel dosing unit 13 to the internal combustion engine 10.

The particle sensor 20 may in this case also be arranged behind the exhaust gas purification system 16 in the flow direction of the exhaust gas, which offers advantages in terms of homogenization of the exhaust gas flow at this position and, in particular, is the case during use in the scope of on-board diagnosis. The devices shown allow observation of the particle output of the internal combustion engine 10 and prognosis of the loading of the exhaust gas purification system 16 configured as a diesel particle filter (DPF).

Figure 2:
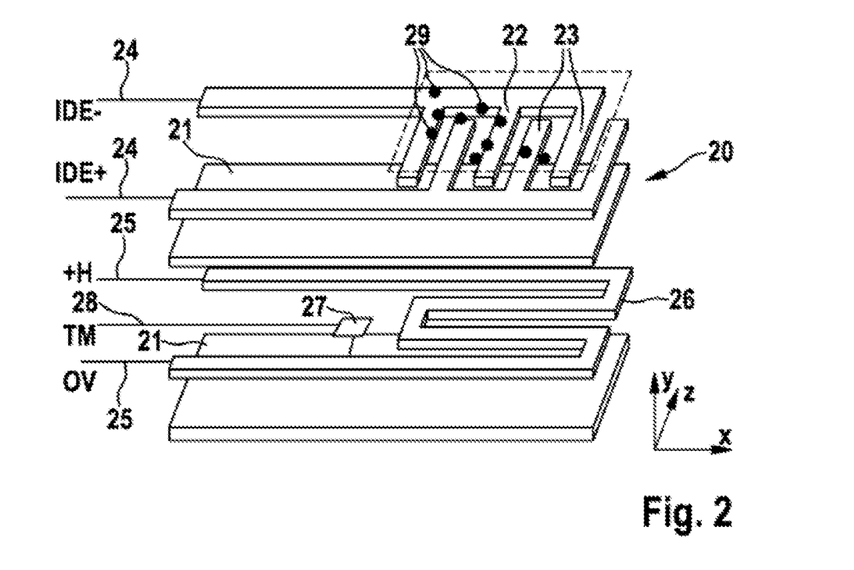

FIG. 2 shows a schematic representation of a particle sensor 20 corresponding to the prior art in an exploded representation.

An IDE measurement structure 22 in the form of a first electrode and a second electrode is applied on insulating carrier layers 21, for example consisting of aluminum oxide. The electrodes are configured in the form of two interdigital comb electrodes engaging in one another, and are referred to as IDE electrodes 23. At the far ends of the IDE electrodes 23, the IDE terminals 24 (IDE+ and IDE−) are provided, by means of which the IDE electrodes 23 are connected to the voltage supply and for carrying out the measurement to the control and evaluation unit 30 (not represented in FIG. 2). In addition, in the example shown, a heating element 26, which is connected by means of additional heating element terminals 25 (H+, OV) to the control and evaluation unit 30, is integrated between the insulating carrier layers 21.

In order to measure the temperature, a temperature sensor 27 may additionally be provided in the layer structure of the particle sensor 20, in which case a temperature sensor terminal 28 (TM) is additionally led out of the particle sensor 20. For example, resistor structures consisting of platinum may be used as a temperature sensor 27. As an alternative, at least a part of the structure of the heating element 26 may also be used as a temperature sensor 27. A coordinate system is furthermore represented schematically in FIG. 2 for orientation of ion migrations in various types of operation.

If such a particle sensor 20 is operated in a gas flow carrying soot particles 29, for example in an exhaust gas channel of a diesel engine or of a firing system, then soot particles 29 from the gas flow are deposited on the particle sensor 20. These have a certain electrical conductivity. In this case, the rate of deposition of the soot particles 29 on the particle sensor 20 depends, besides the particle concentration in the exhaust gas, inter alia also on the voltage which is applied to the IDE electrodes 23. By the applied voltage, an electric field is generated which exerts a corresponding attraction on electrically charged soot particles 29. By suitable selection of the voltage applied to the IDE electrodes 23, the rate of deposition of the soot particles 29 can therefore be influenced.

In the exemplary embodiment, the IDE electrodes 23 and the top insulating carrier layer 21, on which the IDE electrodes 23 are located, are coated with a protective layer. This optional protective layer protects the IDE electrodes 23 from corrosion at the high operating temperatures of the particle sensor 20 which usually prevail. In the present exemplary embodiment, it is made of a material having a low conductivity, although it may also be made of an insulator.

Soot particles 29 from the gas flow have deposited in the form of a layer on the protective layer. Because of the protective layer with low conductivity, the soot particles 29 form a conductive path between the IDE electrodes 23, so that a resistance change takes place between the IDE electrodes 23, depending on the amount of soot particles 29 deposited. This may, for example, be measured by applying a constant voltage to the IDE terminals 24 of the IDE electrodes 23 and determining the change in the current due to the deposited soot particles 29. If the protective layer is configured to be insulating, then the deposited soot particles 29 lead to a change in the impedance of the particle sensor 20, which can be evaluated by a corresponding measurement, preferably with an AC voltage.

If the particle sensor 20 is loaded with a layer of soot particles 29 to such an extent that additionally deposited soot particles 29 do not lead to any further change in the resistance or the impedance of the particle sensor 20, then the particle sensor 20 is regenerated in a regeneration phase. To this end, the particle sensor 20 is heated with the aid of the heating element 26 to such an extent that the deposited soot particles 29 are burnt. In a first phase after the regeneration, when only a few soot particles 29 are deposited on the particle sensor 20, a meaningful resistance or impedance measurement is not possible. Only after a sufficiently long time are enough soot particles 29 once more deposited on the particle sensor 20 so that a closed current path is formed between the IDE electrodes 23 via the soot particles 29 and a measurement becomes possible. Known evaluation methods determine the time after regeneration until a predetermined threshold of the measurement signal is reached, for example a predetermined current value, in order to determine information about the particle concentration in the gas flow. Alternative methods use the rate of change of the signal after a minimum signal is reached, in order to determine the particle concentration.

Figure 3:
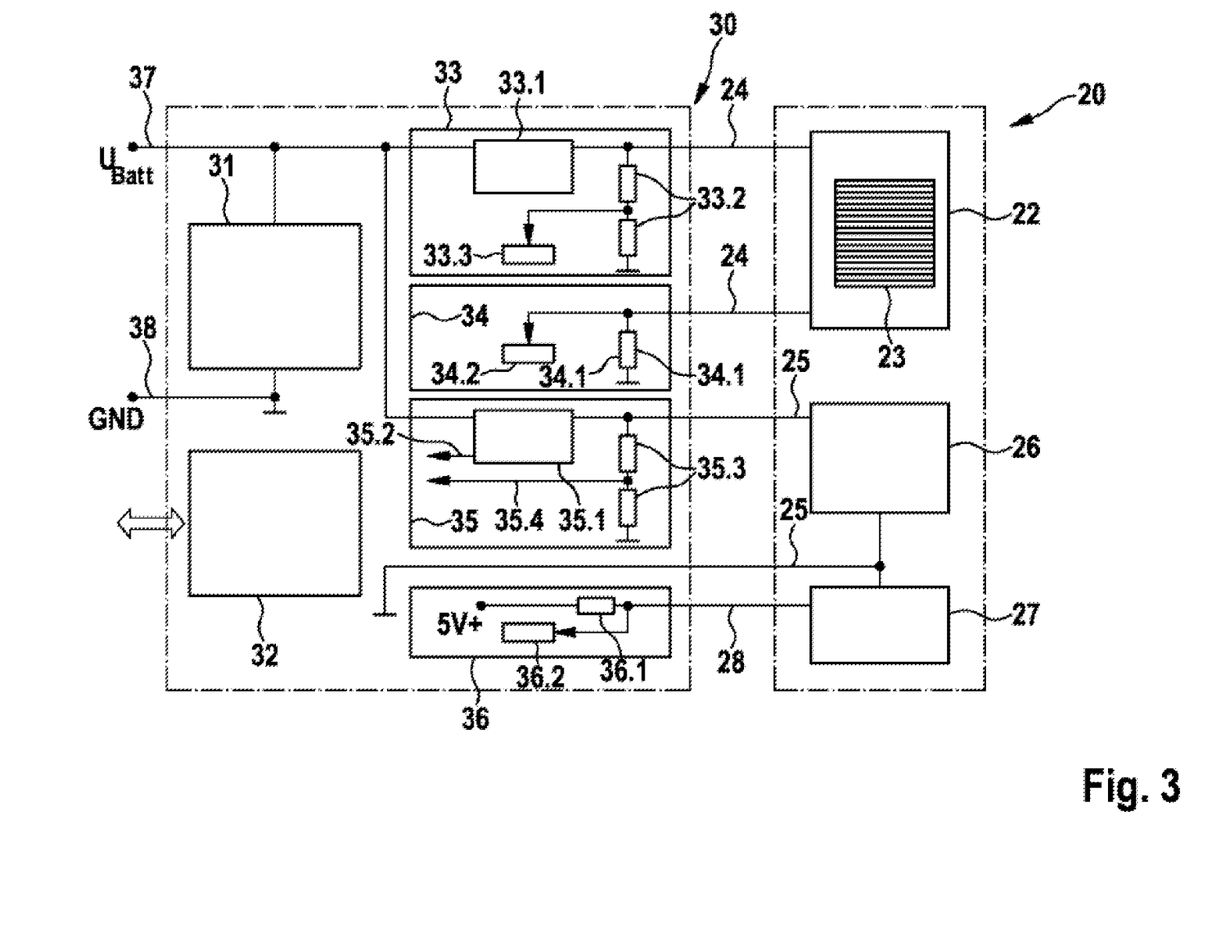
FIG. 3 shows a control and evaluation unit which is connected to the particle sensor.

FIG. 3 schematically represents a block diagram of the interaction of the control and evaluation unit 30 with the particle sensor 20.

The control and evaluation unit 30 (SCU) comprises as essential functional blocks a voltage monitoring unit 31, a CAN bus interface 32, an IDE supply unit 33, an IDE measurement unit 34, a heating element supply unit 35 and a temperature measurement unit 36, and is supplied with electricity by means of a supply voltage 37 $U_{bat}$ and a ground 38.

The IDE measurement structure 22, the heating element 26 and the temperature sensor 27 are represented schematically in the particle sensor 20, the IDE measurement structure 22 with its interdigital electrodes being connected via the IDE terminals 24 to the IDE supply unit 31, and the IDE measurement unit 34 and the heating element 26 being connected via the heating element terminals 25 to the heating element supply unit 35. The temperature sensor 27 is connected via the temperature sensor terminal 28 to the temperature measurement unit 36, the heating element 26 and the temperature sensor 27 sharing a common ground terminal.

The IDE supply unit 33 comprises an IDE voltage source 33.1, with which the potential of one IDE electrode 23 can be adjusted, as well as a voltage divider 33.2, via which, by means of an analog/digital converter 33.3, the potential of this IDE electrode 23 can be measured, digitized and delivered to a μ-controller (not represented here). The IDE measurement unit 34 comprises an input resistor 34.1 via which, by means of another analog/digital converter 34.2, the potential of the other IDE electrode 23 of the IDE measurement structure 22 can be measured, digitized and delivered to the μ-controller for further processing.

The heating element supply unit 35 comprises a switch 35.1, with which the heating element 26 can be switched. The switch 35.1 additionally has an ADC signal output 35.2, via which a heating element status 43 (see FIGS. 4 to 9) can be detected by means of a further analog/digital converter. Provision is additionally made that the heating element voltage $U_H$ can be measured by means of a further voltage divider 35.3 and the measured value can be delivered via a μC signal output 35.4 to the μ-controller for evaluation.

The temperature measurement unit 36 has a constant supply voltage (for example +5 V). A measurement resistor 36.1 forms, with the temperature sensor 27 of the particle sensor 20, a temperature-dependent voltage divider, the voltage potential between these resistors being delivered to a further analog/digital converter 36.2 for digitization and further processing in the μ-controller.

FIGS. 4 to 9 show in various profile diagrams 40 the profile of the temperature 41 of the particle sensor 20 as a function of time 42 for a typical regeneration cycle of the particle sensor 20. Furthermore, in a tabular region of FIGS. 4 to 9, for various time slots, a heating element status 43, i.e. whether the heating element 26 of the particle sensor 20 is switched on or off, a heating element voltage 44 and an IDE voltage difference 45 between the IDE electrodes 23 and the respective electrode potentials IDE+ and IDE− 46, 47 are shown, distinction being made in respect of the time slots between a heating phase 48, a main soot burning phase 49, a diagnostic phase 50 and a newly introduced polarization reversal phase 51 and a cooling phase 52.

Figure 4:
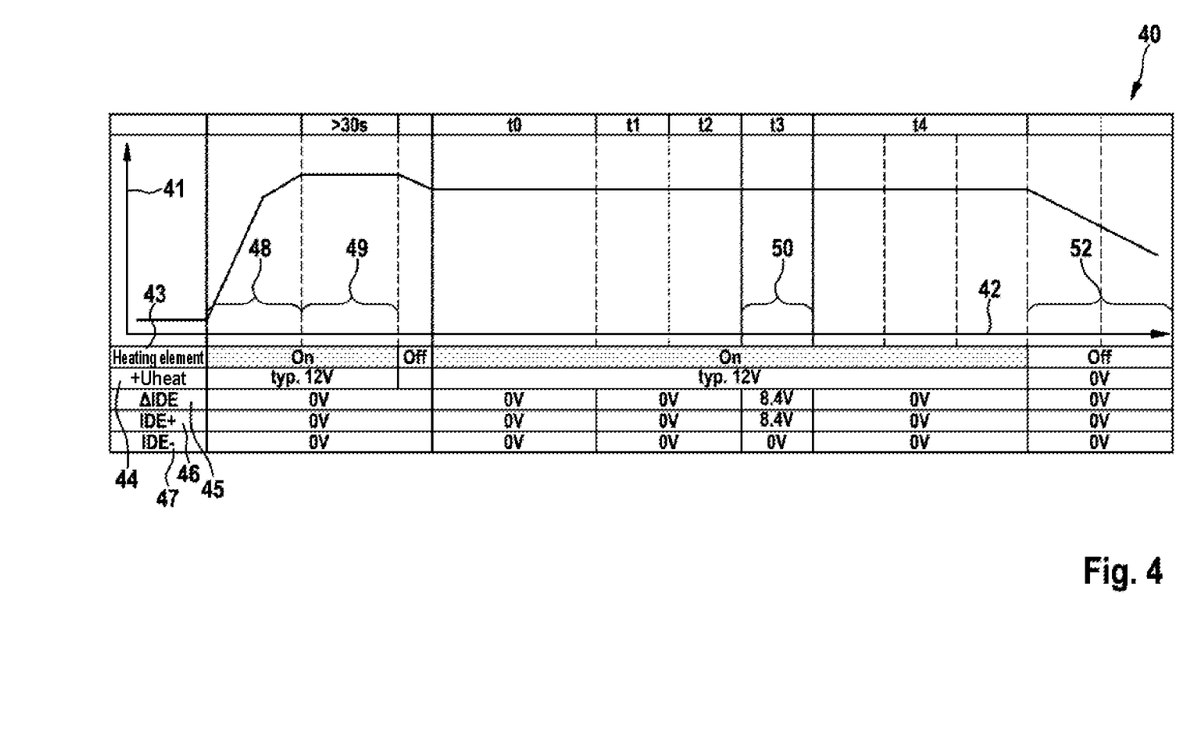
FIGS. 4 to 9 show profile diagrams for various operating modes of the particle sensor.

FIG. 4 shows in the profile diagram 40 the temperature profile and the various potentials according to the prior art. It shows, for example for use in an automobile, the electrical potentials at the IDE electrodes 23 and at the heating element 26 during the regeneration until the start of the actual soot collection phase, as are represented in FIG. 4. It is clear that the heating element potential, the heating element voltage 44 (typically 12 V), except for very short phases, is always higher than the two electrode potentials IDE+, IDE− 46, 47, which during the diagnostic phase may assume a typical value of +8.4 V at the IDE+ electrode. It is furthermore clear that there are long phases with a driving force for the Na$^+$ ions toward the surface and short phases with a driving force toward the negative electrode during the diagnostic phase 50, both of which are repeated cyclically.

With the method according to the invention, with the aid of additional software modules in the control and evaluation unit 30 (SCU), further operating phases of the particle sensor 20 are introduced, without the existing hardware as schematically represented in FIG. 3 having to be adapted.

Figure 5:
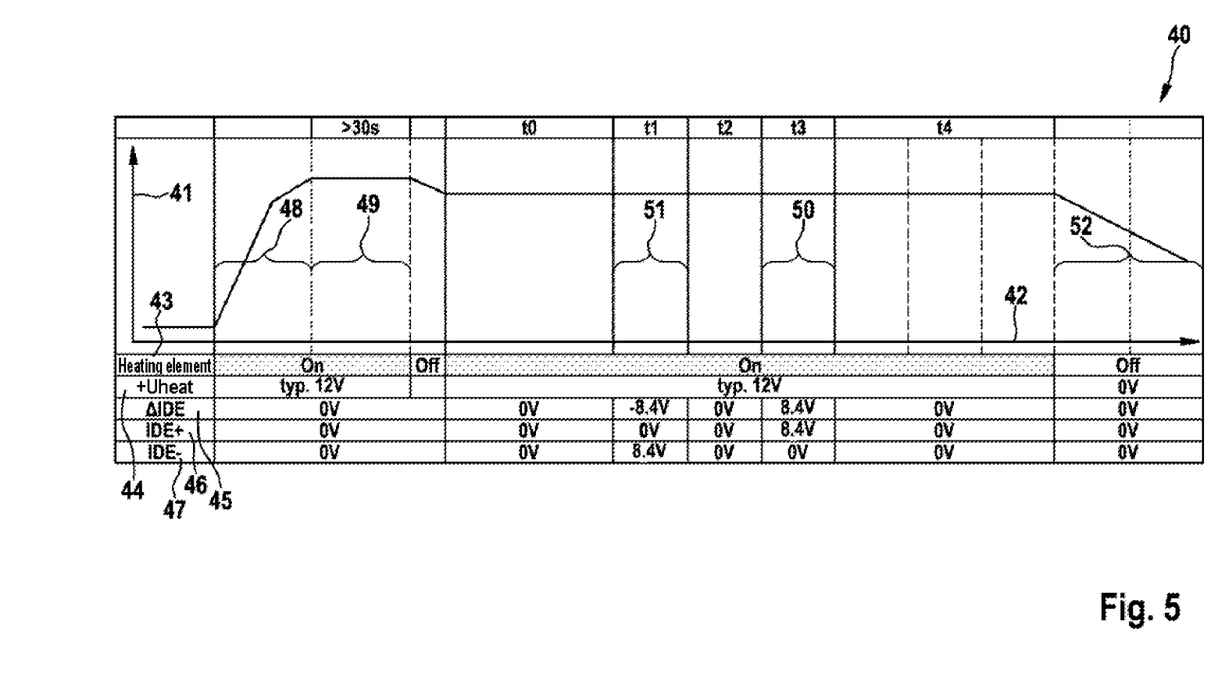

One type of operation allows, during the additionally introduced polarization reversal phase 51, potential reversal for the IDE electrodes 23, as is represented in the profile diagram 40 in FIG. 5, so that there is a voltage difference of typically −8.4 V between the IDE electrodes 23 for the duration $t_1$ of the polarization reversal phase 51. The negative IDE voltage difference means that the negative electrode temporarily lies at 8.4 V and the positive electrode at 0 V. Before the diagnosis, i.e. during the period $t_2$, a phase with a voltage of zero volts at both electrodes may preferably be introduced, as shown in FIG. 5. Since high heating powers are required in the regeneration phase, the PWM duty cycle is very high. The heating element voltage is mainly at 12 V. The very short off phases are in this case neglected.

Because of the reversal pulse, the Na$^+$ ions over the entire region of the IDE measurement structure 22 of the particle sensor 20 can be displaced deliberately toward the positive IDE electrode 23 (IDE+). This is effective particularly in the insulation layer between the electrode fingers of the negative IDE electrode 23 (IDE−) and the positive IDE electrode 23 (IDE+) on the surface and in the layers near the surface. The duration may in principle be selected freely. In order not to significantly lengthen the overall cycle time of the particle sensor 20, however, brief reversal pulses with a duration of <1 s should be used. Because of the small spacings of the electrode fingers, this time is sufficient. The return polarization by repoling and the polarization during the self-diagnosis should compensate for one another. The reversal pulse therefore preferably has a duration equal to the duration of the self-diagnosis. In this case, it is also possible, as is known from DE 10 2009 028 239 A1, to carry out brief repolings during the self-diagnosis (diagnostic phase 50), so that polarization effects during the current measurement and therefore false measurements can be avoided.

According to the invention, further operating phases may be introduced by variable electrode potentials IDE+ or IDE− 46, 47 according to the examples represented in FIGS. 6 to 9, so that new or different electrical potential conditions can be generated in the particle sensor 20 during the regeneration phase.

The positive heating element potential is in this case equally high as or lower than the electrode potential IDE+ 46, so that the driving force for the cations, i.e. essentially the $Na^+$ ions, points in the desired direction, according to FIG. 2 from the surface back into the bulk of the particle sensor 20 (in the −y direction), or so that the cations do not experience a driving force and therefore remain at the previous position. Since the regeneration phases typically last between 30 and 90 s, a comparatively longer period of time is available for this type of operation and its variants. The polarization reversal described in FIG. 5 during the polarization reversal phase 51 may in this case also be integrated during this time.

Figure 6:
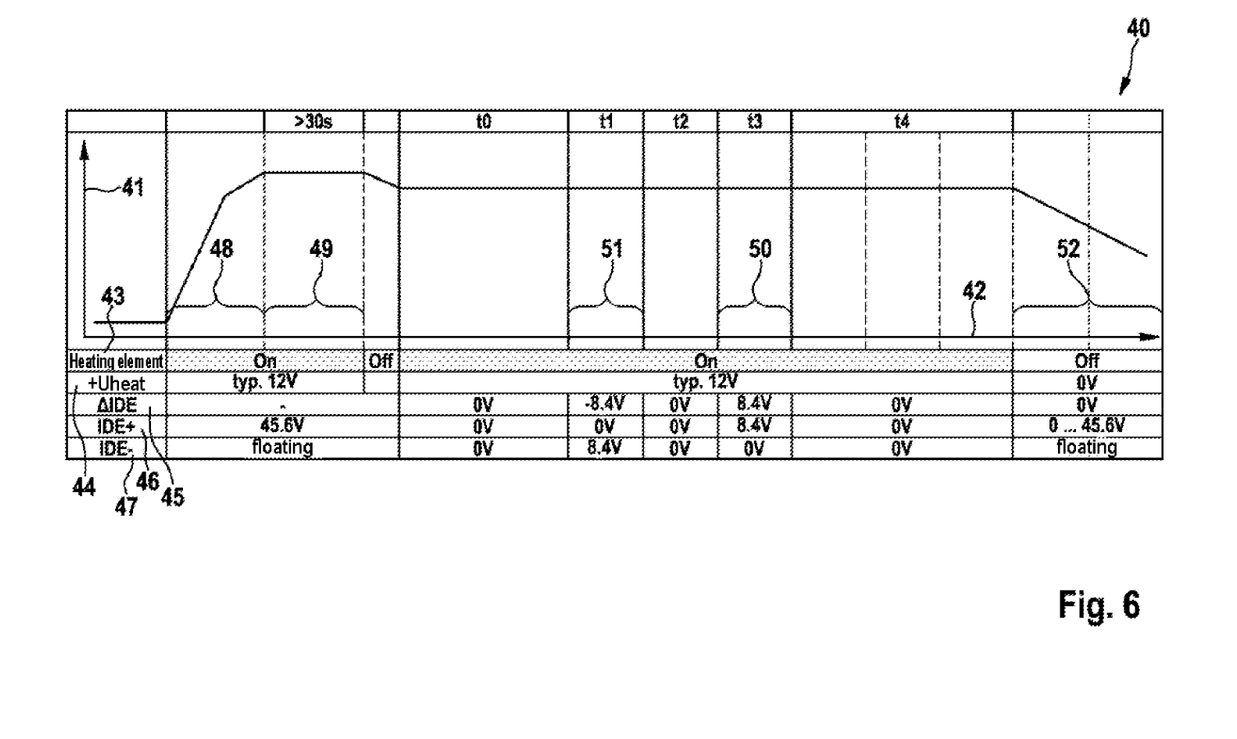
Figure 7:
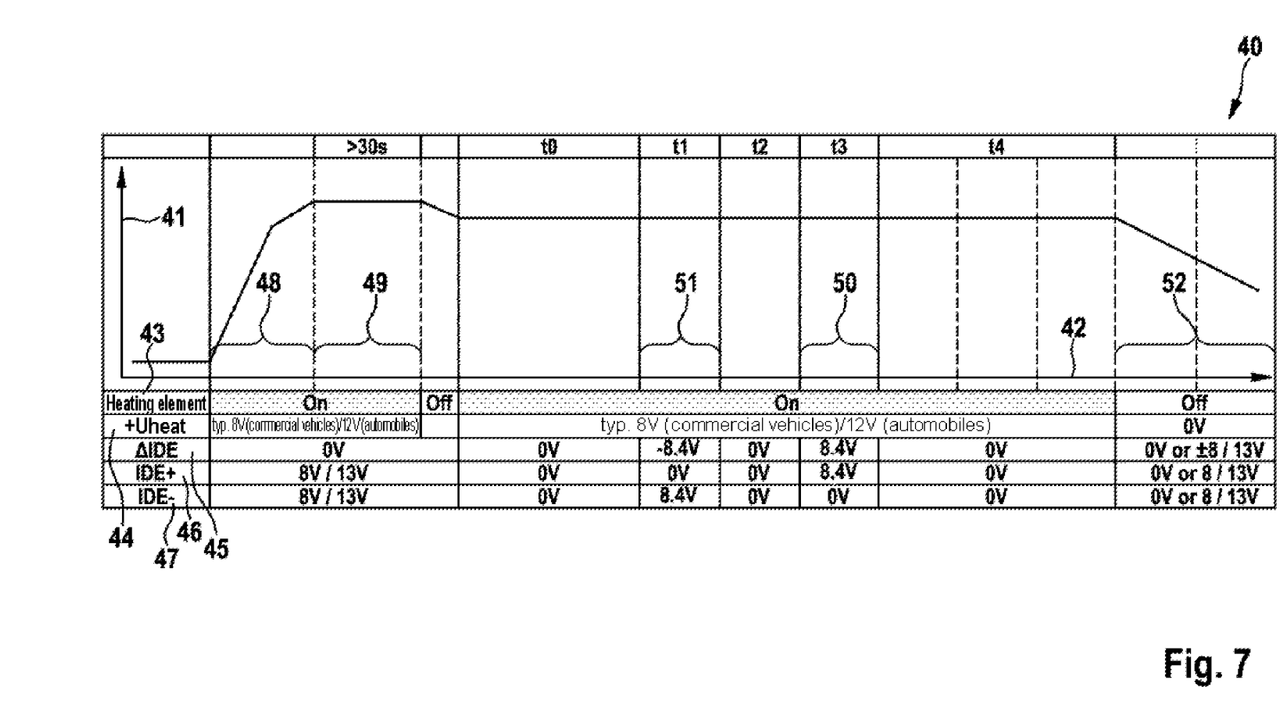
Figure 8:
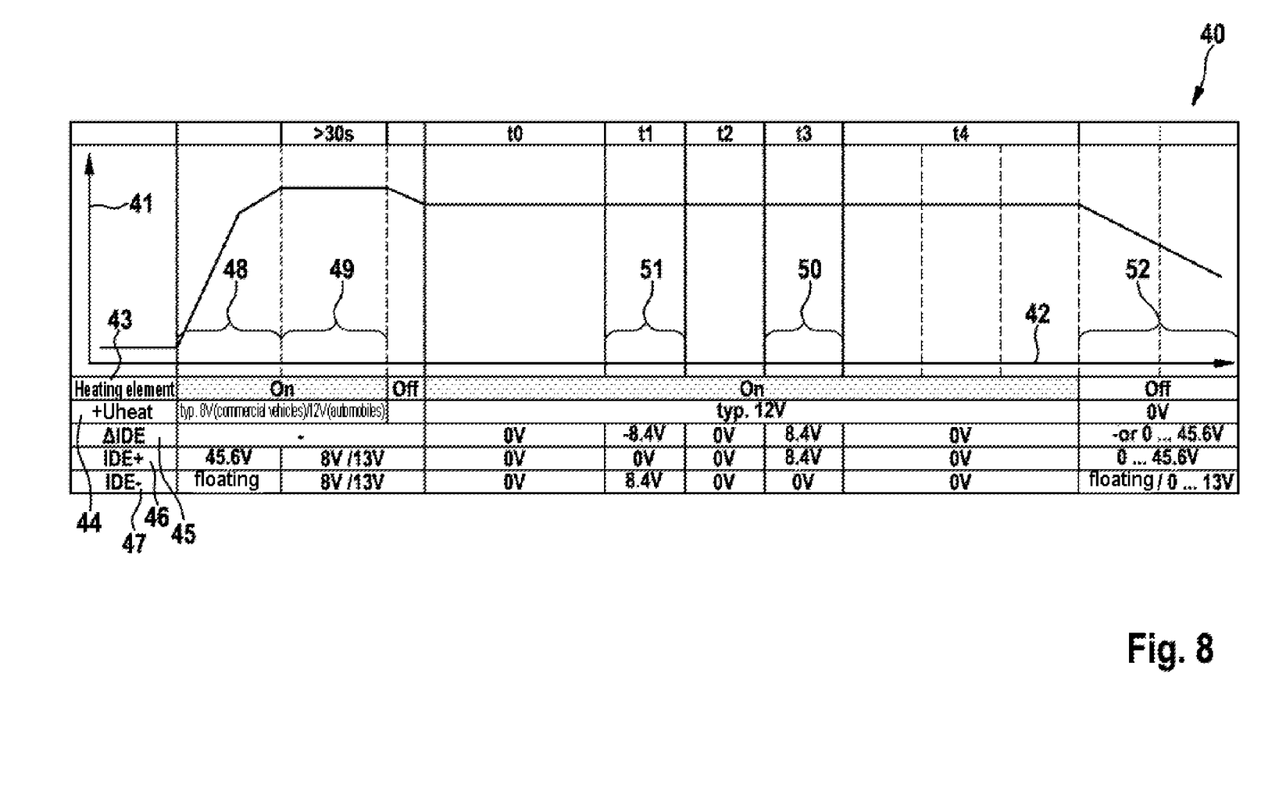

During this phase, the ions may deliberately either be kept at their position, or driven back into the bulk from the surface and optionally also from the bulk to the surface. This may be achieved with a profile fixed in advance or, as according to one variant of the method, it may also be done as a function of the present state in the region of the electrodes, for example as a function of the present diagnostic current. Ultimately, a setpoint concentration or a setpoint range of sodium ions in the region of the electrodes and layers near the surface can therefore be adjusted. This may be variable as a function of time, so that preferably there is a sufficient concentration near the surface to provide the required conductivity only for the time during the self-diagnosis, and otherwise the ions are displaced back into the bulk. In the case of excess introduction of ions, measurable by means of the diagnostic current, these may be driven deeper into the bulk and kept there. FIGS. 6, 7 and 8 show corresponding examples in which, during the regeneration phase, here during the heating phase 48 and the main soot burning phase 49, different electrode potentials IDE+ and IDE− 46, 47 are specified, in which case different electrode potentials IDE+ and IDE− 46, 47 may also be specified in the profile after the heating element 26 is switched off to 0 V in the cooling phase 52. In this case, the time slots $t_0$ to $t_4$ indicated are typically very much shorter than 30 s, i.e. the time scale is not represented linearly or true to scale here. The heating element voltage 44 may typically be 12 V for automobiles and 8 V for commercial vehicles.

Figure 9:
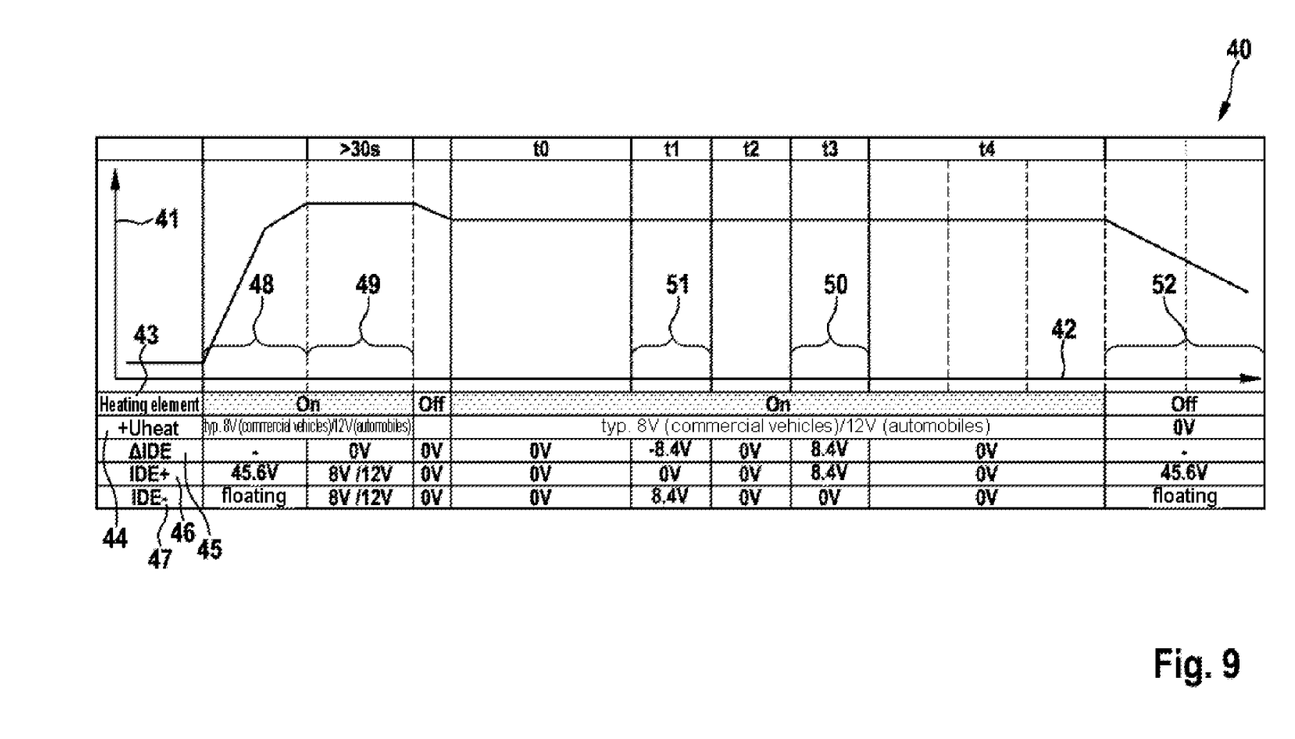

A particularly advantageous method variant is shown by FIG. 9 with a time-adapted profile. During the heating phase 48, the $Na^+$ ions are initially driven into the bulk of the particle sensor by the selected potential settings. This is done by applying a very high electrode potential IDE+ 46 of about 45.6 V, the electric potential IDE− 47 being freely floating. During the subsequent soot burning phase 49, a voltage of 8 V (commercial vehicles) or 12 V (automobiles) is applied to the two electrodes. The effect achievable by this is that the $Na^+$ ions are kept in the bulk. The effect achievable by a subsequent change of the two electric potentials to 0 V is that the $Na^+$ ions can briefly be displaced in the direction of the surface. By the polarization reversal phase 51 following later, enough $Na^+$ ions are accumulated near the surface so that the current can be measured without errors during the diagnostic phase 50. After the end of the regeneration phase (heating element off), as at the start of the regeneration phase, during the heating phase 48 a high electrode potential IDE+ 46 of about 45.6 V is applied, the electrode potential IDE− 47 being freely floating. In this way, the $Na^+$ ions are driven into the bulk of the particle sensor, so that leaching as mentioned in the introduction, and therefore excessive sensor ageing, can be prevented.

Besides the four examples represented in FIGS. 6 to 9, further possibilities may be envisioned, for example alternating operation with one or more pulses of typically 8 to 13 V or 45.6 V at the IDE+ electrode with a potential of 0 V in between, in which case the pulse length may also be adjusted as a function of a diagnostic current measured. Furthermore, voltage potentials different to zero volts as described for the other phase during the regeneration at the IDE electrodes may also be applied intermittently or permanently during the periods t0 and t4. The types of operation described above according to FIG. 5 and FIGS. 6 to 9 may be applied individually or in combination.

The invention claimed is:

1. A method for operating a particle sensor (20) in order to determine a particle content in a gas flow, wherein the particle sensor (20) comprises on its surface at least two interdigital IDE electrodes (23) engaging one another and a heating element (26), separated from the IDE electrodes (23) by an insulation layer and by which, in a regeneration phase, the particle sensor (20) is heated and a soot load on the particle sensor (20) is thereby be removed, and with which, in a diagnostic phase (50) during the regeneration phase, a current is measured by intermittently applying a measurement voltage to the IDE electrodes (23) and, with the aid of a profile and strength of the current as a function of time, a functional test of the particle sensor (20) is carried out, wherein, during the regeneration phase, additional operating phases are introduced in which, outside the diagnostic phase (50), ions are deliberately displaced by intermittently applying certain voltage potentials to the IDE electrodes (23); wherein in further operating phases during the regeneration phase, outside the diagnostic phase (50) and a polarization reversal phase (51), the electrical potentials of the IDE electrodes (23) are set to be equal to or greater than a heating element voltage (44) at the heating element (26).

2. The method as claimed in claim 1, characterized in that, for a predeterminable time during the polarization reversal phase (51) preceding the diagnostic phase (50), a positive voltage potential is applied to the negative IDE electrode (23), the positive IDE electrode (23) being at a ground potential.

3. The method as claimed in claim 2, characterized in that a duration which corresponds at most to the duration of the diagnostic phase (50) is selected for the polarization reversal phase (51).

4. The method as claimed in claim 1, characterized in that, during these operating phases, the negative IDE electrode (23) is switched between a floating voltage potential and a voltage potential higher than the positive heating element voltage (44), and the positive IDE electrode (23) is operated during this time with a voltage potential equal to or higher than the positive heating element voltage (44).

5. The method as claimed in claim 1, characterized in that the voltage potential at the positive IDE electrode (23) is between 8 and 13 volts.

6. The method as claimed in claim 1, characterized in that the voltage potentials at the IDE electrodes (23), with the exception of the diagnostic phase (50) and the polarization reversal phase (51), are applied throughout the entire regeneration phase.

7. The method as claimed in claim 1, characterized in that, in terms of the voltage potentials applied to the IDE electrodes (23) and duration, the additional operating phases within the regeneration phase of the particle sensor (20) are fixed in advance.

8. The method as claimed in claim 1 wherein the on-board diagnosis of the particle sensor (20), arranged in the exhaust gas system (17) of an internal combustion engine (1) configured as a diesel engine, performs on-board diagnosis of a particle filter.

9. The method as claimed in claim 1, characterized in that the voltage potential at the positive IDE electrode (23) is more than 40 volts.

10. The method as claimed in claim 1, characterized in that the voltage potentials at the IDE electrodes (23), with the exception of the diagnostic phase (50) and the polarization reversal phase (51), are applied intermittently.

11. The method as claimed in claim 1, characterized in that, in terms of the voltage potentials applied to the IDE electrodes (23) and duration, the additional operating phases within the regeneration phase of the particle sensor (20) are adapted as a function of the present state of the IDE electrodes (23).

12. The method as claimed in claim 1, wherein the on-board diagnosis of the particle sensor (20), arranged in the exhaust gas system (17) of an internal combustion engine (1) configured as a diesel engine, measures soot emissions.

13. The method as claimed in claim 1, wherein the on-board diagnosis of the particle sensor (20), arranged in the exhaust gas system (17) of an internal combustion engine (1) configured as an Otto engine, performs on-board diagnosis of a particle filter.

14. The method as claimed in claim 1, wherein the on-board diagnosis of the particle sensor (20), arranged in the exhaust gas system (17) of an internal combustion engine (1) configured as an Otto engine, measures soot emissions.

15. A device for operating a particle sensor (20) in order to determine a particle content in a gas flow, wherein the particle sensor (20) comprises on its surface at least two interdigital IDE electrodes (23) engaging one another and a heating element (26), which is separated from the IDE electrodes (23) by an insulation layer and by which, in a regeneration phase, the particle sensor (20) is heated by a control and evaluation unit (30) and a soot load on the particle sensor (20) is thereby removed, and with which, in a diagnostic phase (50) during the regeneration phase, a current is measured by intermittently applying a measurement voltage to the IDE electrodes (23) and, with the aid of a profile and strength of this current as a function of time, a functional test of the particle sensor (20) is carried out, characterized in that the control and evaluation unit (30) comprises an IDE supply unit (33), an IDE measurement unit (34), a heating element supply unit (35) and a temperature measurement unit (36), for carrying out the method as claimed in claim 1.

16. A method for operating a particle sensor (20) in order to determine a particle content in a gas flow, wherein the particle sensor (20) comprises on its surface at least two interdigital IDE electrodes (23) engaging one another and a heating element (26), separated from the IDE electrodes (23) by an insulation layer and by which, in a regeneration phase, the particle sensor (20) is heated and a soot load on the particle sensor (20) is thereby be removed, and with which, in a diagnostic phase (50) during the regeneration phase, a current is measured by intermittently applying a measurement voltage to the IDE electrodes (23) and, with the aid of a profile and strength of the current as a function of time, a functional test of the particle sensor (20) is carried out, wherein, during the regeneration phase, additional operating phases are introduced in which, outside the diagnostic phase (50), ions are deliberately displaced by intermittently applying certain voltage potentials to the IDE electrodes (23); wherein for a predeterminable time during a polarization reversal phase (51) preceding the diagnostic phase (50), a positive voltage potential is applied to the negative IDE electrode (23), the positive IDE electrode (23) being at a ground potential.

17. The method as claimed in claim 16, characterized in that a duration which corresponds at most to the duration of the diagnostic phase (50) is selected for the polarization reversal phase (51).

\* \* \* \* \*